United States Patent [19]
Yaver et al.

[11] Patent Number: 5,693,510
[45] Date of Patent: Dec. 2, 1997

[54] **GENE ENCODING CARBOXYPEPTIDASE OF *ASPERGILLUS NIGER***

[75] Inventors: Debbie Sue Yaver; Sheryl Ann Thompson, both of Davis, Calif.

[73] Assignee: Novo Nordisk Biotech, Inc., Davis, Calif.

[21] Appl. No.: 608,452

[22] Filed: Feb. 28, 1996

Related U.S. Application Data

[62] Division of Ser. No. 309,341, Sep. 20, 1994, Pat. No. 5,594,119.

[51] Int. Cl.$^6$ .............................. C12N 15/00; C12N 1/14; C12N 1/16; C12N 1/18
[52] U.S. Cl. .................... 435/172.3; 435/254.11; 435/254.3; 435/255.1; 435/256.1
[58] Field of Search ..................... 435/172.3, 254.11, 435/254.3, 255.1, 256.1

[56] References Cited

FOREIGN PATENT DOCUMENTS

WO 92/17595  10/1992  WIPO.

OTHER PUBLICATIONS

Sørensen et al., Carlsberg Res. Commun., vol. 54, pp. 193–202 (1989).
Jarai et al., Gene, vol. 145, pp. 171–178 (1994).
Frederick et al., Gene, vol. 125, pp. 57–64 (1993).
Svendsen et al., FEBS Letters, vol. 333, No. 1,2, pp. 39–43 (1993).
Woolford et al., Molecular & Cellular Biology, vol. 6, No. 7, pp. 2500–2510 (1986).
Mukhtar et al., Gene, vol. 121, pp. 173–177 (1992).
Ammerer et al., Molecular & Cellular Biology, vol. 6, No. 7, pp. 2490–2499 (1986).
Stevens et al., J. of Cell Biology, vol. 102, pp. 1551–1557 (1986).
Rodney Rothstein, Methods in Enzymology, vol. 194, pp. 281–301 (1991).
L. Valls et al., Cell, vol. 48, pp. 887–897 (1987).
Berka et al., Gene, vol. 86, No. 2, pp. 153–162 (1990).
Yaver et al., 34th Annual Meeting of ASCB, Molecular Biol. Cell, 5 (Suppl.) ISSN: 1059–1525 (1994).
Dal Degan et al. (1992) Appl. and Environ. Microbiol. 58(7): 2144–2152.
de Ruiter–Jacobs et al. (1989) Curr. Genetics 16: 159–163.
Krishnan et al. (1986) J. Chromatog. 370: 315–326.

*Primary Examiner*—Robert A. Wax
*Assistant Examiner*—Lisa J. Hobbs
*Attorney, Agent, or Firm*—Steve T. Zelson, Esq.; Elias J. Lambiris, Esq.

[57] ABSTRACT

The present invention relates to a gene encoding an ascomycete or deuteromycete carboxypeptidase Y gene, and host cells modified so as to produce reduced amounts of carboxypeptidase.

11 Claims, 13 Drawing Sheets

FIG. IA

```
                         10              20              30              40              50              60
              TCCTCTGCCT  ACTCATCCCA  TCACCATCTC  AATTCATACC  GCCCCCGTGG  GGTTTCAGCA  CCA
              >
              69                      78                      87                      96                      105                     114
              ATG AGA GTC CTT CCA GCT GCT ATG GTT CTG GGA GCG GCC ACG GCC GTT CCT
              MET Arg Val Leu Pro Ala Ala MET Val Leu Gly Ala Ala Thr Ala Val Pro 123                     132                     141                     150                     159                     168
              CCC TTC CAG CAG CTT GGA GTC AAC GGT GCC AAG CAC GGT GCC GAC CAT GCG
              Pro Phe Gln Gln Val Leu Gly Asn Gly Ala Lys His Gly Ala Asp His Ala 177                     186                     195                     204                     213                     222
              GCC GAG GTC CCT GCG GAT CAC AGT GCC GAC GGG TTC TCC AAG CCG CTG CAC GCA
              Ala Glu Val Pro Ala Asp His Ser Ala Asp Gly Phe Ser Lys Pro Leu His Ala 231                     240                     249                     258                     267                     276
              CAG GAG GAG CTG AAG TCT CTC TCT GAC GAG GCT CGT AAG CTT TGG GAT GAG
              Gln Glu Glu Leu Lys Ser Leu Ser Asp Glu Ala Arg Lys Leu Trp Asp Glu 285                     294                     303                     312                     321                     330
              TTC CCG GAG ATG AGC ATG GAT CAG AAC CCT CTC TTC TCC CTC CCC
              Phe Pro Glu Ser MET Asp Gln Asn Pro Leu Phe Ser Leu Pro

GTG GCC AGC TTC TTT
              Val Ala Ser Phe Phe
```

FIG. 1B

```
      339        348            357            366            375            384
      |          |              |              |              |              |
      AAG  CAC  AAC  CGC  CGT  CCC  GAC  TCG  CAC  TGG  GAC  CAC  ATC  GTC  CGC  GGC  TCC
      Lys  His  Asn  Arg  Arg  Pro  Asp  Ser  His  Trp  Asp  His  Ile  Val  Arg  Gly  Ser 393            402            411            420            429            438
      |              |              |              |              |              |
      GAC  GTT  CAG  AGC  GTC  TGG  GTC  ACT  GGT  GAG  AAC  GGT  GAG  AAG  GAG  CGC  GAG  GTC
      Asp  Val  Gln  Ser  Val  Trp  Val  Thr  Gly  Glu  Asn  Gly  Glu  Lys  Glu  Arg  Glu  Val 447            456            465            474            483            492
      |              |              |              |              |              |
      GAT  GGC  AAG  CTG  GAA  GCC  TAT  GAT  CTC  AGG  GTC  AAG  AAG  ACC  GAT  CCT  GGC  TCT
      Asp  Gly  Lys  Leu  Glu  Ala  Tyr  Asp  Leu  Arg  Val  Lys  Lys  Thr  Asp  Pro  Gly  Ser 501            510            519            528            537            546
      |              |              |              |              |              |
      CTT  GGC  ATC  GAC  CCC  GGC  GTG  AAG  CAG  TAC  ACC  GGT  TAT  CTC  GAT  GAC  AAC  GAG
      Leu  Gly  Ile  Asp  Pro  Gly  Val  Lys  Gln  Tyr  Thr  Gly  Tyr  Leu  Asp  Asp  Asn  Glu 555            564                                                        611
      |              |                                                          |
      AAT  GAT  AAG  CAT  TTG  TTC  TAC  T  GTAAGCACAC  CTTGGTTCAA  GATCACGCTT  TTTATATGCT
      Asn  Asp  Lys  His  Leu  Phe  Tyr  Trp 621            631            641            650            659            668
      |              |              |              |              |              |
      CTGGATATCT  AACGCAACTT  AG  GG  TTC  GAG  TCT  CGC  AAT  GAC  CCC  GAG  AAT  GAT
                                    Phe  Phe  Glu  Ser  Arg  Asn  Asp  Pro  Glu  Asn  Asp 581            591            601
```

FIG. IC

| 677 | | | | | | | | 722 |
|---|---|---|---|---|---|---|---|---|
| CCC | GTT | CTG | TGG | CTG | AAC | GGT | CCT | GGG | TGC | TCT | CTC | ACC | GGT | CTC |
| Pro | Val | Leu | Trp | Leu | Asn | Gly | Pro | Gly | Cys | Ser | Leu | Thr | Gly | Leu |

| 731 | | | | | | | | 776 |
| TTC | ATG | GAG | CTT | GGC | CCT | AGC | AGC | ATC | AAC | AAG | ATC | CAG | CCG | GTC | TAC | AAT |
| Phe | MET | Glu | Leu | Gly | Pro | Ser | Ser | Ile | Asn | Lys | Ile | Gln | Pro | Val | Tyr | Asn |

| 785 | | | | | | | | 830 |
| GAC | TAC | GCT | TGG | AAC | TCC | AAC | GCG | TCC | GTG | ATC | CTT | GAC | CAG | CCT | GTC | AAT |
| Asp | Tyr | Ala | Trp | Asn | Ser | Asn | Ala | Ser | Val | Ile | Phe | Leu | Asp | Gln | Pro | Val | Asn |

| 839 | | | | | | | | 884 |
| GTC | GGT | TAC | TCC | TAC | AGT | AAC | TCT | GCT | GTC | AGC | GAC | ACG | GTC | GCT | GCT | GGC | AAG |
| Val | Gly | Tyr | Ser | Tyr | Ser | Asn | Ser | Ala | Val | Ser | Asp | Thr | Val | Ala | Ala | Gly | Lys |

| 893 | | | | | | | | 938 |
| GAC | GTC | TAT | GCC | TTG | ACC | CTC | TTC | AAA | CAA | TTC | CCC | GAG | TAT | GCT | AAG |
| Asp | Val | Tyr | Ala | Leu | Thr | Leu | Phe | Lys | Gln | Phe | Pro | Glu | Tyr | Ala | Lys |

| 947 | | | | | | | | 992 |
| CAG | GAC | TTC | CAC | ATT | GCC | GGT | GAA | TCT | TAT | GCT | GGT | CAC | TAT | ATC | CCC | GTC | TTC |
| Gln | Asp | Phe | His | Ile | Ala | Gly | Glu | Ser | Tyr | Ala | Gly | His | Tyr | Ile | Pro | Val | Phe |

FIG. 1D

```
       1001        1010        1019        1028        1037        1046
       |           |           |           |           |           |
       GCT TCG GAG ATC CTG TCT CAC AAG AAG CGC AAC ATC AAC CTG CAG TCC GTT CTC
       Ala Ser Glu Ile Leu Ser His Lys Lys Arg Asn Ile Asn Leu Gln Ser Val Leu 1055        1064        1073        1082        1091        1100
                   |           |           |           |           |           |
       ATT GGC AAC GGT CTC ACC GAC GGA TAC ACC CAG TAC GAG TAC TAC CGT CCC ATG
       Ile Gly Asn Gly Leu Thr Asp Gly Tyr Thr Gln Tyr Glu Tyr Tyr Arg Pro MET 1109        1118        1127        1136        1145        1154
                   |           |           |           |           |           |
       GCC TGC GGT GAC GGC GGT TAC CCA GCT GTC TTG GAC GAG AGC TCC TGC CAG TCC
       Ala Cys Gly Asp Gly Gly Tyr Pro Ala Val Leu Asp Glu Ser Ser Cys Gln Ser 1163        1172        1181        1190        1199        1208
                   |           |           |           |           |           |
       ATG GAC AAC GCT CTT CCT CGC TGC CAG TCT ATG ATT GAG TCT TGC TAC AGT TCC
       MET Asp Asn Ala Leu Pro Arg Cys Gln Ser MET Ile Glu Ser Cys Tyr Ser Ser 1217        1226        1235        1244        1253        1262
                   |           |           |           |           |           |
       GAG AGC GCT TGG GTT TGT GTC CCG GCC TCC ATC TAC TGT AAC AAC GCC CTC CTT
       Glu Ser Ala Trp Val Cys Val Pro Ala Ser Ile Tyr Cys Asn Asn Ala Leu Leu 1271        1280        1289        1298        1307        1316
                   |           |           |           |           |           |
       GCC CCT TAC CAG CGC ACT GGG CAG AAC GTC TAT GAT GTC CGT GGT AAG TGC GAG
       Ala Pro Tyr Gln Arg Thr Gly Gln Asn Val Tyr Asp Val Arg Gly Lys Cys Glu
```

FIG. 1E

```
      1325         1334         1343         1352         1361         1370
   |            |            |            |            |            |
GAT AGC TCT AAC CTT TGC TAC TCG GCT ATG GGC TAC GTC AGC GAC TAC CTG AAC
Asp Ser Ser Asn Leu Cys Tyr Ser Ala MET Gly Tyr Val Ser Asp Tyr Leu Asn 1379         1388         1397         1406         1415         1424
   |            |            |            |            |            |
AAG CCC GAA GTC ATC GAG GCT GTT GGC GCT GAG GTC AAC GGC TAC GAC TCG TGC
Lys Pro Glu Val Ile Glu Ala Val Gly Ala Glu Val Asn Gly Tyr Asp Ser Cys 1433         1442         1451         1460         1469         1478
   |            |            |            |            |            |
AAC TTT GAC ATC AAC CGC AAC TTC CTC TTC CAC GGT GAC TGG ATG AAG CCC TAC
Asn Phe Asp Ile Asn Arg Asn Phe Leu Phe His Gly Asp Trp MET Lys Pro Tyr 1487         1496         1505         1514         1523         1532
   |            |            |            |            |            |
CAC CGC CTC GTT CCG GGA CTC CTG GAG CAG ATC CCT GTC TTG ATC TAT GCC GGT
His Arg Leu Val Pro Gly Leu Leu Glu Gln Ile Pro Val Leu Ile Tyr Ala Gly 1541         1550         1559         1568         1577         1586
   |            |            |            |            |            |
GAT GCT GAT TTC ATT TGC AAC TGG CTG GGC AAC AAG GCC TGG ACT GAA GCC CTG
Asp Ala Asp Phe Ile Cys Asn Trp Leu Gly Asn Lys Ala Trp Thr Glu Ala Leu 1595         1604         1613         1622         1631         1640
   |            |            |            |            |            |
GAG TGG CCC GGA CAG GCT GAA TAT GCC TCC GCT GAG CTG GAG GAT CTG GTC ATT
Glu Trp Pro Gly Gln Ala Glu Tyr Ala Ser Ala Glu Leu Glu Asp Leu Val Ile
```

FIG. 1F

```
             1649       1658       1667       1676       1685       1694
         GTC GAC AAT GAG CAC ACG GGC AAG AAG ATT GGC CAG GTT AAG TCC CAT GGC AAC
         Val Asp Asn Glu His Thr Gly Lys Lys Ile Gly Gln Val Lys Ser His Gly Asn 1703       1712       1721       1730       1739       1748
         TTC ACC TTC ATG CGT CTC TAT GGT GGT GGC CAC ATG GTC CCG ATG GAC CAG CCC
         Phe Thr Phe MET Arg Leu Tyr Gly Gly Gly His MET Val Pro MET Asp Gln Pro 1757       1766       1775       1784       1793       1809
         GAG TCG AGT CTC GAG TTC TTC AAC CGC TGG TTG GGA GGT GAA TGG TTC TAA AGACGTGCTA
         Glu Ser Ser Leu Glu Phe Phe Asn Arg Trp Leu Gly Gly Glu Trp Phe 1819       1829       1839       1849       1859       1869       1879
CCACCGCATA TAGACTTTCT GGTCATTTCG GTGACACTGC AGATATGTTT CTTAACGATA GTTTGAGCAT 1889       1899       1909       1919       1929       1939       1949
GCTTGTCAAT GCCCACTAGT CCCGATCCTT ATATGTTGCA TGGTATCTAT GAGTTTGTC ACTATAGTGC 1959       1969       1979       1989       1999       2009       2019
ATTATACATG TGTACTTCGT ATGAGAATGA ATCGATCGCA TTTACACGCA TATAAATAGT ACCCACCTCC 2029       2039       2049       2059       2068
GCCTGGACAT GAATTAGGCC CGGCCAGTCG TTTACATACA GTGCTAGAA
```

FIG. 2A

```
         10         20         30         40         50         60         70
GCGGCCGCTG CTACTTGCTT TTTCTAATTT GATACTTTTG TGTCCGTACC GTACCTTCCA GACCGCAAGG 80         90        100        110        120        130    139
TACCCATCCT CTACCTACTC ATCCCATCAT CATCTCGATT TCATACCAAC CCGTTGGGT TTCAACACA
```

```
                                                                start of propeptide
                                                                    1  ↓   193
    148          157          166          175          184          GCG GCC GTC CCT
>   ATG  AGA  GTT  CTT  CCA  GCT  GCT  ATG  CTG  GTT  GGA  GCG  GGC  ACT  GCC  GTC  CCT
    MET  Arg  Val  Leu  Pro  Ala  Ala  MET  Leu  Val  Gly  Ala  Gly  Thr  Ala  Val  Pro 202          211          220          229          238          247
    CCC  TTC  CAG  CAG  GTC  CTT  GGA  GGT  AAC  GGT  GCC  AAG  CAC  GGT  GCC  GAC  CAT  GCG
    Pro  Phe  Gln  Gln  Val  Leu  Gly  Gly  Asn  Gly  Ala  Lys  His  Gly  Ala  Asp  His  Ala 256          265          274          283          292          301
    GCC  GAG  GTC  CCT  GCG  GAT  CAC  AGT  GCC  GAC  GGG  TTC  TCC  AAG  CCG  CTG  CCG  GCA
    Ala  Glu  Val  Pro  Ala  Asp  His  Ser  Ala  Asp  Gly  Phe  Ser  Lys  Pro  Leu  His  Ala 310          319          328          337          346          355
    GCC  GAG  GAG  CTG  AAG  TCT  CTC  GAT  GAG  GCT  CGT  AAG  CTC  TGG  GAT  GAG
    Phe  Gln  Glu  Glu  Leu  Lys  Ser  Leu  Asp  Glu  Ala  Arg  Lys  Leu  Trp  Asp  Glu
```

FIG. 2B

```
      364       373       382       391       400       409
      |         |         |         |         |         |
GTT   GCT   AGC   TTC   TTC   CCG   GAG   AGC   ATG   GAT   CAG   AAC   CCT   CTC   TTC   TCC   CTC   CCC
Val   Ala   Ser   Phe   Phe   Pro   Glu   Ser   MET   Asp   Gln   Asn   Pro   Leu   Phe   Ser   Leu   Pro 418       427       436       445       454       463
                |         |         |         |         |         |
AAG   AAG   AAC   CGC   AAC   CCC   GAC   CAC   CAC   TGG   GAC   CAC   ATC   GTC   CGC   GGC   TCC
Lys   Lys   Asn   Arg   Arg   Pro   Asp   His   His   Trp   Asp   His   Ile   Val   Arg   Gly   Ser 472       481       490       499       508       517
                |         |         |         |         |         |
GAC   GTT   CAG   AGC   GTC   TGG   GTT   ACT   GGT   GAG   AAC   GGT   GAG   AAG   GAG   CGT   GAG   GTC
Asp   Val   Gln   Ser   Val   Trp   Val   Thr   Gly   Glu   Asn   Gly   Glu   Lys   Glu   Arg   Glu   Val
                                                                     predicted N-teminus of mature CPY
                526       535       544       553↓      562       571
                |         |         |         |         |         |
GAT   GGC   AAG   CTG   GAA   GCC   TAT   GAT   CTC   AGG   GTC   AAG   AAG   ACC   GAT   CCT   AGC   TCT
Asp   Gly   Lys   Leu   Glu   Ala   Tyr   Asp   Leu   Arg   Val   Lys   Lys   Thr   Asp   Pro   Ser   Ser 580       589       598       607       616       625
                |         |         |         |         |         |
CTT   GGC   ATC   GAC   CCT   GGC   GTA   AAG   CAG   TAC   ACC   GGT   TAT   CTC   GAT   GAC   AAC   GAG
Leu   Gly   Ile   Asp   Pro   Gly   Val   Lys   Gln   Tyr   Thr   Gly   Tyr   Leu   Asp   Asp   Asn   Glu
```

FIG. 2C

|  |  |  |  |  |  | 679 |
|---|---|---|---|---|---|---|
| 634 | 643 | 652 | 661 | 670 | | |
| AAC GAC<br>Asn Asp | AAG CAT CTG<br>Lys His Leu | TTC TAC TGG<br>Phe Tyr Trp | TTC GAG TCT<br>Phe Glu Ser | CGC AAT GAC<br>Arg Asn Asp | CCC GAG AAT<br>Pro Glu Asn |  |
| 688 | 697 | 706 | 715 | 724 | | 733 |
| GAC CCT<br>Asp Pro | GTT GTT CTG<br>Val Val Leu | TGG CTG AAC<br>Trp Leu Asn | GGT GGC CCT<br>Gly Gly Pro | GGA TGC TCC<br>Gly Cys Ser | CTC ACC GGT<br>Leu Thr Gly |  |
| 742 | 751 | 760 | 769 | 778 | | 787 |
| CTT TTC ATG<br>Leu Phe MET | GAG CTC GGC<br>Glu Leu Gly | CCT AGC AGC<br>Pro Ser Ser | ATC AAC AAG<br>Ile Asn Lys | AAG ATC CAG<br>Lys Ile Gln | CCG GTC TAC<br>Pro Val Tyr |  |
| 796 | 805 | 814 | 823 | 832 | | 841 |
| AAC GAC TAC<br>Asn Asp Tyr | GCT TGG AAC<br>Ala Trp Asn | TCC AAC GCG<br>Ser Asn Ala | TCC GTG ATC<br>Ser Val Ile | TTC CTT GAC<br>Phe Leu Asp | CAG CCT GTC<br>Gln Pro Val |  |
| 850 | 859 | 868 | 877 | 886 | | 895 |
| AAC GAC<br>Asn Asp | GGT TAC TCT<br>Gly Tyr Ser | TAC AGC AAC<br>Tyr Ser Asn | TCT GCT GTC<br>Ser Ala Val | GAC ACC GTT<br>Asp Thr Val | GCT GGC<br>Ala Gly |  |
| 904 | 913 | 922 | 931 | 940 | | 949 |
| AAG GAC<br>Lys Asp | GTC TAT GCC<br>Val Tyr Ala | CTC TTC TTC<br>Leu Phe Phe | ACC AAA CAA<br>Thr Lys Gln | TTC CCC GAG<br>Phe Pro Glu | TAT GCC<br>Tyr Ala |  |
|  |  |  |  |  | | |
| | CTT CTT ACC<br>Leu Leu Thr | TTG CTT ACC<br>Leu Leu Thr | TTC ACC AAA<br>Phe Thr Lys | | | |

FIG. 2D

```
      958        967        976        985        994       1003
AAG   CAG   GAC   TTC   CAC   ATT   GCC   GGT   TCC   GAA   TAT   GCT   GGT   CAC   TAT   ATC   CCC   GTC
Lys   Gln   Asp   Phe   His   Ile   Ala   Gly   Ser   Glu   Tyr   Ala   Gly   His   Tyr   Ile   Pro   Val 1012       1021       1030       1039       1048       1057
TTT   GCT   TCG   GAG   ATT   TTG   TCT   CAC   AAG   AAG   CGC   AAC   ATC   AAC   CTG   CAG   TCC   GTT
Phe   Ala   Ser   Glu   Ile   Leu   Ser   His   Lys   Lys   Arg   Asn   Ile   Asn   Leu   Gln   Ser   Val 1066       1075       1084       1093       1102       1111
CTT   ATT   GGC   AAC   GGT   CTC   GAC   GGT   CTC   ACT   CAG   TAC   GAG   TAC   CGT   CCC
Leu   Ile   Gly   Asn   Gly   Leu   Asp   Gly   Leu   Thr   Gln   Tyr   Glu   Tyr   Arg   Pro 1120       1129       1138       1147       1156       1165
ATG   GCC   TGT   GGT   GAC   GGT   GGT   TAC   CCA   GCT   GTC   TTG   GAC   GAG   GGC   TCC   TGC   CAG
MET   Ala   Cys   Gly   Asp   Gly   Gly   Tyr   Pro   Ala   Val   Leu   Asp   Glu   Gly   Ser   Cys   Gln 1174       1183       1192       1201       1210       1219
GCC   ATG   GAC   AAC   GCC   CTT   CCT   CGC   TGC   CAG   TCT   ATG   ATT   GAG   TCT   TGC   TAT   AGT
Ala   MET   Asp   Asn   Ala   Leu   Pro   Arg   Cys   Gln   Ser   MET   Ile   Glu   Ser   Cys   Tyr   Ser 1228       1237       1246       1255       1264       1273
GCC   TGT   GTT   GTC   CCG   GCC   TCC   ATC   TAC   TGT   AAC   GCC   CTC
Cys   Val   Cys   Val   Pro   Ala   Ser   Ile   Tyr   Cys   Asn   Ala   Leu

TCC   GAG   AGC   GCT   TGG
Ser   Glu   Ser   Ala   Trp   Val
```

FIG. 2E

| 1282 | 1291 | 1300 | 1309 | 1318 | 1327 |
| CTT | GCC | CCT | TAC | CAG | AAC | CGC | ACC | GGA | CAG | AAC | GTC | TAC | GAT | GTT | CGT | GGT | AAG | TGC |
| Leu | Ala | Pro | Tyr | Gln | Arg | Thr | Gly | Gln | Asn | Val | Tyr | Asp | Val | Arg | Gly | Lys | Cys |

| 1336 | 1345 | 1354 | 1363 | 1372 | 1381 |
| GAG | GAT | AGC | TCC | AAC | CTC | TGC | TAC | TCG | GCC | ATG | GGC | TAC | GTC | AGC | GAC | TAC | CTG |
| Glu | Asp | Ser | Ser | Asn | Leu | Cys | Tyr | Ser | Ala | MET | Gly | Tyr | Val | Ser | Asp | Tyr | Leu |

| 1390 | 1399 | 1408 | 1417 | 1426 | 1435 |
| AAC | AAG | ACC | GAG | GTC | ATT | GAG | GCT | GTT | GGC | GCT | GAG | GTC | AAC | GGC | TAC | GAC | TCG |
| Asn | Lys | Thr | Glu | Val | Ile | Glu | Ala | Val | Gly | Ala | Glu | Val | Asn | Gly | Tyr | Asp | Ser |

| 1444 | 1453 | 1462 | 1471 | 1480 | 1489 |
| TGC | AAC | TTT | GAC | ATC | AAC | CGC | AAC | CTC | TTC | CAC | GGT | GAC | TGG | ATG | AAG | CCC |
| Cys | Asn | Phe | Asp | Ile | Asn | Arg | Asn | Leu | Phe | His | Gly | Asp | Trp | MET | Lys | Pro |

| 1498 | 1507 | 1516 | 1525 | 1534 | 1543 |
| TAC | CAC | CGT | CTC | GTT | CCG | GGA | CTC | CTG | GAG | CAG | ATC | CCT | GTC | CTG | ATC | TAC | GCT |
| Tyr | His | Arg | Leu | Val | Pro | Gly | Leu | Leu | Glu | Gln | Ile | Pro | Val | Leu | Ile | Tyr | Ala |

| 1552 | 1561 | 1570 | 1579 | 1588 | 1597 |
| GGT | GAC | GCC | GAT | TTC | ATC | TGC | AAC | TGG | CTG | GGC | AAC | AAG | GCC | TGG | ACT | GAA | GCC |
| Gly | Asp | Ala | Asp | Phe | Ile | Cys | Asn | Trp | Leu | Gly | Asn | Lys | Ala | Trp | Thr | Glu | Ala |

FIG.2F

| | 1606 | 1615 | 1624 | 1633 | 1642 | 1651 |
|---|---|---|---|---|---|---|
| CTT | GAG | TGG | CCC | GGA | CAG | GCT | GAA | TAT | GCC | TCC | AAG | CTG | GAG | GAC | CTG | GTC |
| Leu | Glu | Trp | Pro | Gly | Gln | Ala | Glu | Tyr | Ala | Ser | Lys | Leu | Glu | Asp | Leu | Val |

| | 1660 | 1669 | 1678 | 1687 | 1696 | 1705 |
|---|---|---|---|---|---|---|
| GTG | GTC | GAG | AAT | GAG | CAC | AAG | AAG | ATC | GGC | CAG | GTC | AAG | TCC | CAT | GGC |
| Val | Val | Glu | Asn | Glu | His | Lys | Lys | Ile | Gly | Gln | Val | Lys | Ser | His | Gly |

| | 1714 | 1723 | 1732 | 1741 | 1750 | 1759 |
|---|---|---|---|---|---|---|
| AAC | TTC | ACC | TTC | ATG | CGT | CTC | TAT | GGC | GGT | GGC | CAC | ATG | GTC | CCG | ATG | GAC | CAA |
| Asn | Phe | Thr | Phe | MET | Arg | Leu | Tyr | Gly | Gly | Gly | His | MET | Val | Pro | MET | Asp | Gln |

| | 1768 | 1777 | 1786 | 1795 | 1804 | 1813 |
|---|---|---|---|---|---|---|
| CCC | GAG | TCG | AGT | CTT | GAA | TTC | TTC | AAC | CGC | TGG | TTG | GGA | GGT | GAA | TGG | TTT | TAA |
| Pro | Glu | Ser | Ser | Leu | Glu | Phe | Phe | Asn | Arg | Trp | Leu | Gly | Gly | Glu | Trp | Phe |

| 1823 | 1833 | 1843 | 1853 | 1863 | 1873 | 1883 |
|---|---|---|---|---|---|---|
| AGACGTGCTA | TCACCGCATA | TAGACTTTCC | GGTCATTTCG | GTGACACTGC | AGATATGTTT | CTTAACGATA |

| 1893 | 1903 | 1913 | 1923 | 1933 | 1943 | 1953 |
|---|---|---|---|---|---|---|
| GTTTGAGGAT | GCTTGTCAAT | GCCCACTAAT | CCCGAGCCTT | ATGTTACATG | GTATCTATGA | GTTTGTCATT |

| 1963 | 1973 | 1983 | 1993 | 2002 |
|---|---|---|---|---|
| ATAGTGCATT | ATGCATTTGT | ACTCCGTACG | AGAATGAAATC | AGCGGCCGC |

Construct for the disruption of CPY

HindIII (0)
(HindIII/PstI (773))
Aspergillus oryzae pyrG
(HindIII/PstI (1587))
HindIII (6500)

▬ = A. niger CPY gene
▨ = A. oryzae pyrG

* # in parentheses correspond to base pairs in CPY fragment.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 2068 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Aspergillus niger ( i x ) FEATURE:
        ( A ) NAME/KEY: intron
        ( B ) LOCATION: 572..632

( i x ) FEATURE:
    ( A ) NAME/KEY: CDS
    ( B ) LOCATION: join (571..633)

( x i ) SEQUENCE DESCRIPTION: SEQ ID NO: 1:

```
TCCTCTGCCT ACTCATCCCA TCACCATCTC AATTCATACC GCCCCCGTGG GGTTTCAGCA              60

CCA ATG AGA GTC CTT CCA GCT GCT ATG CTG GTT GGA GCG GCC ACG GCG             108
    Met Arg Val Leu Pro Ala Ala Met Leu Val Gly Ala Ala Thr Ala
    1           5                   10                  15

GCC GTT CCT CCC TTC CAG CAG GTC CTT GGA GGT AAC GGT GCC AAG CAC             156
Ala Val Pro Pro Phe Gln Gln Val Leu Gly Gly Asn Gly Ala Lys His
            20              25                  30

GGT GCC GAC CAT GCG GCC GAG GTC CCT GCG GAT CAC AGT GCC GAC GGG             204
Gly Ala Asp His Ala Ala Glu Val Pro Ala Asp His Ser Ala Asp Gly
                35              40              45

TTC TCC AAG CCG CTG CAC GCA TTC CAG GAG GAG CTG AAG TCT CTC TCT             252
Phe Ser Lys Pro Leu His Ala Phe Gln Glu Glu Leu Lys Ser Leu Ser
        50              55                  60

GAC GAG GCT CGT AAG CTT TGG GAT GAG GTG GCC AGC TTC TTC CCG GAG             300
Asp Glu Ala Arg Lys Leu Trp Asp Glu Val Ala Ser Phe Phe Pro Glu
65              70                  75

AGC ATG GAT CAG AAC CCT CTC TTT TCC CTC CCC AAG AAG CAC AAC CGC             348
Ser Met Asp Gln Asn Pro Leu Phe Ser Leu Pro Lys Lys His Asn Arg
80              85                  90                  95

CGT CCC GAC TCG CAC TGG GAC CAC ATC GTC CGC GGC TCC GAC GTT CAG             396
Arg Pro Asp Ser His Trp Asp His Ile Val Arg Gly Ser Asp Val Gln
                100                 105                 110

AGC GTC TGG GTC ACT GGT GAG AAC GGT GAG AAG GAG CGC GAG GTC GAT             444
Ser Val Trp Val Thr Gly Glu Asn Gly Glu Lys Glu Arg Glu Val Asp
        115                 120                 125

GGC AAG CTG GAA GCC TAT GAT CTC AGG GTC AAG AAG ACC GAT CCT GGC             492
Gly Lys Leu Glu Ala Tyr Asp Leu Arg Val Lys Lys Thr Asp Pro Gly
        130                 135                 140

TCT CTT GGC ATC GAC CCC GGC GTG AAG CAG TAC ACC GGT TAT CTC GAT             540
Ser Leu Gly Ile Asp Pro Gly Val Lys Gln Tyr Thr Gly Tyr Leu Asp
        145                 150                 155

GAC AAC GAG AAT GAT AAG CAT TTG TTC TAC GTAAGCACAC CTTGGTTCAA               590
Asp Asn Glu Asn Asp Lys His Leu Phe Tyr
160                 165

GATCACGCTT TTTATATGCT CTGGATATCT AACGCAACTT AG TGG TTC TTC GAG              644
                                                Trp Phe Phe Glu
                                                        170

TCT CGC AAT GAC CCC GAG AAT GAT CCC GTT GTT CTG TGG CTG AAC GGT             692
Ser Arg Asn Asp Pro Glu Asn Asp Pro Val Val Leu Trp Leu Asn Gly
        175                 180                 185

GGC CCT GGG TGC TCT TCC CTC ACC GGT CTC TTC ATG GAG CTT GGC CCT             740
Gly Pro Gly Cys Ser Ser Leu Thr Gly Leu Phe Met Glu Leu Gly Pro
190                 195                 200                 205

AGC AGC ATC AAC AAG AAG ATC CAG CCG GTC TAC AAT GAC TAC GCT TGG             788
Ser Ser Ile Asn Lys Lys Ile Gln Pro Val Tyr Asn Asp Tyr Ala Trp
                210                 215                 220

AAC TCC AAC GCG TCC GTG ATC TTC CTT GAC CAG CCT GTC AAT GTC GGT             836
Asn Ser Asn Ala Ser Val Ile Phe Leu Asp Gln Pro Val Asn Val Gly
                225                 230                 235

TAC TCC TAC AGT AAC TCT GCT GTC AGC GAC ACG GTC GCT GCT GGC AAG             884
Tyr Ser Tyr Ser Asn Ser Ala Val Ser Asp Thr Val Ala Ala Gly Lys
        240                 245                 250

GAC GTC TAT GCC TTG CTT ACC CTC TTC TTC AAA CAA TTC CCC GAG TAT             932
Asp Val Tyr Ala Leu Leu Thr Leu Phe Phe Lys Gln Phe Pro Glu Tyr
        255                 260                 265
```

| | | | | | | | | | | | | | | | | |
|---|---|---|---|---|---|---|---|---|---|---|---|---|---|---|---|---|
| GCT | AAG | CAG | GAC | TTC | CAC | ATT | GCC | GGT | GAA | TCT | TAT | GCT | GGT | CAC | TAT | 980 |
| Ala 270 | Lys | Gln | Asp | Phe | His 275 | Ile | Ala | Gly | Glu | Ser 280 | Tyr | Ala | Gly | His | Tyr 285 | |
| ATC | CCC | GTC | TTC | GCT | TCG | GAG | ATC | CTG | TCT | CAC | AAG | AAG | CGC | AAC | ATC | 1028 |
| Ile | Pro | Val | Phe | Ala 290 | Ser | Glu | Ile | Leu | Ser 295 | His | Lys | Lys | Arg | Asn 300 | Ile | |
| AAC | CTG | CAG | TCC | GTT | CTC | ATT | GGC | AAC | GGT | CTC | ACC | GAC | GGA | TAC | ACC | 1076 |
| Asn | Leu | Gln | Ser 305 | Val | Leu | Ile | Gly | Asn 310 | Gly | Leu | Thr | Asp | Gly 315 | Tyr | Thr | |
| CAG | TAC | GAG | TAC | TAC | CGT | CCC | ATG | GCC | TGC | GGT | GAC | GGC | GGT | TAC | CCA | 1124 |
| Gln | Tyr | Glu 320 | Tyr | Tyr | Arg | Pro | Met 325 | Ala | Cys | Gly | Asp | Gly 330 | Gly | Tyr | Pro | |
| GCT | GTC | TTG | GAC | GAG | AGC | TCC | TGC | CAG | TCC | ATG | GAC | AAC | GCT | CTT | CCT | 1172 |
| Ala | Val | Leu 335 | Asp | Glu | Ser | Ser | Cys 340 | Gln | Ser | Met | Asp | Asn 345 | Ala | Leu | Pro | |
| CGC | TGC | CAG | TCT | ATG | ATT | GAG | TCT | TGC | TAC | AGT | TCC | GAG | AGC | GCT | TGG | 1220 |
| Arg 350 | Cys | Gln | Ser | Met 355 | Ile | Glu | Ser | Cys | Tyr 360 | Ser | Ser | Glu | Ser | Ala 365 | Trp | |
| GTT | TGT | GTC | CCG | GCC | TCC | ATC | TAC | TGT | AAC | AAC | GCC | CTC | CTT | GCC | CCT | 1268 |
| Val | Cys | Val | Pro | Ala 370 | Ser | Ile | Tyr | Cys | Asn 375 | Asn | Ala | Leu | Leu | Ala 380 | Pro | |
| TAC | CAG | CGC | ACT | GGG | CAG | AAC | GTC | TAT | GAT | GTC | CGT | GGT | AAG | TGC | GAG | 1316 |
| Tyr | Gln | Arg | Thr 385 | Gly | Gln | Asn | Val | Tyr 390 | Asp | Val | Arg | Gly | Lys 395 | Cys | Glu | |
| GAT | AGC | TCT | AAC | CTT | TGC | TAC | TCG | GCT | ATG | GGC | TAC | GTC | AGC | GAC | TAC | 1364 |
| Asp | Ser | Ser 400 | Asn | Leu | Cys | Tyr | Ser 405 | Ala | Met | Gly | Tyr | Val 410 | Ser | Asp | Tyr | |
| CTG | AAC | AAG | CCC | GAA | GTC | ATC | GAG | GCT | GTT | GGC | GCT | GAG | GTC | AAC | GGC | 1412 |
| Leu | Asn | Lys 415 | Pro | Glu | Val | Ile 420 | Glu | Ala | Val | Gly | Ala 425 | Glu | Val | Asn | Gly | |
| TAC | GAC | TCG | TGC | AAC | TTT | GAC | ATC | AAC | CGC | AAC | TTC | CTC | TTC | CAC | GGT | 1460 |
| Tyr 430 | Asp | Ser | Cys | Asn | Phe 435 | Asp | Ile | Asn | Arg | Asn 440 | Phe | Leu | Phe | His | Gly 445 | |
| GAC | TGG | ATG | AAG | CCC | TAC | CAC | CGC | CTC | GTT | CCG | GGA | CTC | CTG | GAG | CAG | 1508 |
| Asp | Trp | Met | Lys | Pro 450 | Tyr | His | Arg | Leu | Val 455 | Pro | Gly | Leu | Leu | Glu 460 | Gln | |
| ATC | CCT | GTC | TTG | ATC | TAT | GCC | GGT | GAT | GCT | GAT | TTC | ATT | TGC | AAC | TGG | 1556 |
| Ile | Pro | Val | Leu 465 | Ile | Tyr | Ala | Gly | Asp 470 | Ala | Asp | Phe | Ile | Cys 475 | Asn | Trp | |
| CTG | GGC | AAC | AAG | GCC | TGG | ACT | GAA | GCC | CTG | GAG | TGG | CCC | GGA | CAG | GCT | 1604 |
| Leu | Gly | Asn 480 | Lys | Ala | Trp | Thr | Glu 485 | Ala | Leu | Glu | Trp | Pro 490 | Gly | Gln | Ala | |
| GAA | TAT | GCC | TCC | GCT | GAG | CTG | GAG | GAT | CTG | GTC | ATT | GTC | GAC | AAT | GAG | 1652 |
| Glu | Tyr 495 | Ala | Ser | Ala | Glu | Leu 500 | Glu | Asp | Leu | Val | Ile 505 | Val | Asp | Asn | Glu | |
| CAC | ACG | GGC | AAG | AAG | ATT | GGC | CAG | GTT | AAG | TCC | CAT | GGC | AAC | TTC | ACC | 1700 |
| His | Thr | Gly 510 | Lys | Lys | Ile | Gly 515 | Gln | Val | Lys | Ser | His 520 | Gly | Asn | Phe | Thr 525 | |
| TTC | ATG | CGT | CTC | TAT | GGT | GGT | GGC | CAC | ATG | GTC | CCG | ATG | GAC | CAG | CCC | 1748 |
| Phe | Met | Arg | Leu 530 | Tyr | Gly | Gly | Gly | His 535 | Met | Val | Pro | Met | Asp 540 | Gln | Pro | |
| GAG | TCG | AGT | CTC | GAG | TTC | TTC | AAC | CGC | TGG | TTG | GGA | GGT | GAA | TGG | TTC | 1796 |
| Glu | Ser | Ser | Leu 545 | Glu | Phe | Phe | Asn | Arg 550 | Trp | Leu | Gly | Gly | Glu 555 | Trp | Phe | |

TAA AGACGTGCTA CCACCGCATA TAGACTTTCT GGTCATTTCG GTGACACTGC  1849

AGATATGTTT CTTAACGATA GTTGAGCAT GCTTGTCAAT GCCCACTAGT CCCGATCCTT  1909

ATATGTTGCA TGGTATCTAT GAGTTTTGTC ACTATAGTGC ATTATACATG TGTACTTCGT  1969

ATGAGAATGA ATCGATCGCA TTTACACGCA TATAAATAGT ACCCACCTCC GCCTGGACAT  2029

GAATTAGGCC CGGCCAGTCG TTTACATACA GTGCTAGAA                                     2068

( 2 ) INFORMATION FOR SEQ ID NO: 2:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 2:

```
Met Arg Val Leu Pro Ala Ala Met Leu Val Gly Ala Ala Thr Ala Ala
 1           5                  10                  15
Val Pro Pro Phe Gln Gln Val Leu Gly Gly Asn Gly Ala Lys His Gly
            20                  25                  30
Ala Asp His Ala Ala Glu Val Pro Ala Asp His Ser Ala Asp Gly Phe
             35                 40                  45
Ser Lys Pro Leu His Ala Phe Gln Glu Glu Leu Lys Ser Leu Ser Asp
 50                     55                  60
Glu Ala Arg Lys Leu Trp Asp Glu Val Ala Ser Phe Phe Pro Glu Ser
 65                 70                  75                  80
Met Asp Gln Asn Pro Leu Phe Ser Leu Pro Lys Lys His Asn Arg Arg
                85                  90                  95
Pro Asp Ser His Trp Asp His Ile Val Arg Gly Ser Asp Val Gln Ser
            100                 105                 110
Val Trp Val Thr Gly Glu Asn Gly Glu Lys Glu Arg Glu Val Asp Gly
            115                 120                 125
Lys Leu Glu Ala Tyr Asp Leu Arg Val Lys Lys Thr Asp Pro Gly Ser
    130                 135                 140
Leu Gly Ile Asp Pro Gly Val Lys Gln Tyr Thr Gly Tyr Leu Asp Asp
145                 150                 155                 160
Asn Glu Asn Asp Lys His Leu Phe Tyr Trp Phe Phe Glu Ser Arg Asn
                165                 170                 175
Asp Pro Glu Asn Asp Pro Val Val Leu Trp Leu Asn Gly Gly Pro Gly
            180                 185                 190
Cys Ser Ser Leu Thr Gly Leu Phe Met Glu Leu Gly Pro Ser Ser Ile
            195                 200                 205
Asn Lys Lys Ile Gln Pro Val Tyr Asn Asp Tyr Ala Trp Asn Ser Asn
    210                 215                 220
Ala Ser Val Ile Phe Leu Asp Gln Pro Val Asn Val Gly Tyr Ser Tyr
225                 230                 235                 240
Ser Asn Ser Ala Val Ser Asp Thr Val Ala Ala Gly Lys Asp Val Tyr
                245                 250                 255
Ala Leu Leu Thr Leu Phe Phe Lys Gln Phe Pro Glu Tyr Ala Lys Gln
            260                 265                 270
Asp Phe His Ile Ala Gly Glu Ser Tyr Ala Gly His Tyr Ile Pro Val
    275                 280                 285
Phe Ala Ser Glu Ile Leu Ser His Lys Lys Arg Asn Ile Asn Leu Gln
    290                 295                 300
Ser Val Leu Ile Gly Asn Gly Leu Thr Asp Gly Tyr Thr Gln Tyr Glu
305                 310                 315                 320
Tyr Tyr Arg Pro Met Ala Cys Gly Asp Gly Gly Tyr Pro Ala Val Leu
```

|       |       |       |       |       |       |       |       |       |       |       |       |       |       |
|-------|-------|-------|-------|-------|-------|-------|-------|-------|-------|-------|-------|-------|-------|
|       |       |       | 325   |       |       |       | 330   |       |       |       | 335   |       |       |
| Asp   | Glu   | Ser   | Ser   | Cys   | Gln   | Ser   | Met   | Asp   | Asn   | Ala   | Leu   | Pro   | Arg   | Cys | Gln |
|       |       |       | 340   |       |       |       |       | 345   |       |       |       | 350   |       |
| Ser   | Met   | Ile   | Glu   | Ser   | Cys   | Tyr   | Ser   | Ser   | Glu   | Ser   | Ala   | Trp   | Val   | Cys | Val |
|       |       |       | 355   |       |       |       | 360   |       |       |       | 365   |       |       |
| Pro   | Ala   | Ser   | Ile   | Tyr   | Cys   | Asn   | Asn   | Ala   | Leu   | Leu   | Ala   | Pro   | Tyr   | Gln | Arg |
|       | 370   |       |       |       |       | 375   |       |       |       |       | 380   |       |       |
| Thr   | Gly   | Gln   | Asn   | Val   | Tyr   | Asp   | Val   | Arg   | Gly   | Lys   | Cys   | Glu   | Asp   | Ser | Ser |
| 385   |       |       |       |       | 390   |       |       |       |       | 395   |       |       |       |     | 400 |
| Asn   | Leu   | Cys   | Tyr   | Ser   | Ala   | Met   | Gly   | Tyr   | Val   | Ser   | Asp   | Tyr   | Leu   | Asn | Lys |
|       |       |       |       | 405   |       |       |       |       | 410   |       |       |       |       | 415 |     |
| Pro   | Glu   | Val   | Ile   | Glu   | Ala   | Val   | Gly   | Ala   | Glu   | Val   | Asn   | Gly   | Tyr   | Asp | Ser |
|       |       |       | 420   |       |       |       |       | 425   |       |       |       |       | 430   |     |     |
| Cys   | Asn   | Phe   | Asp   | Ile   | Asn   | Arg   | Asn   | Phe   | Leu   | Phe   | His   | Gly   | Asp   | Trp | Met |
|       |       |       | 435   |       |       |       | 440   |       |       |       |       | 445   |       |     |     |
| Lys   | Pro   | Tyr   | His   | Arg   | Leu   | Val   | Pro   | Gly   | Leu   | Leu   | Glu   | Gln   | Ile   | Pro | Val |
|       | 450   |       |       |       |       | 455   |       |       |       |       | 460   |       |       |     |     |
| Leu   | Ile   | Tyr   | Ala   | Gly   | Asp   | Ala   | Asp   | Phe   | Ile   | Cys   | Asn   | Trp   | Leu   | Gly | Asn |
| 465   |       |       |       |       | 470   |       |       |       |       | 475   |       |       |       |     | 480 |
| Lys   | Ala   | Trp   | Thr   | Glu   | Ala   | Leu   | Glu   | Trp   | Pro   | Gly   | Gln   | Ala   | Glu   | Tyr | Ala |
|       |       |       |       | 485   |       |       |       |       | 490   |       |       |       |       | 495 |     |
| Ser   | Ala   | Glu   | Leu   | Glu   | Asp   | Leu   | Val   | Ile   | Val   | Asp   | Asn   | Glu   | His   | Thr | Gly |
|       |       |       | 500   |       |       |       |       | 505   |       |       |       |       | 510   |     |     |
| Lys   | Lys   | Ile   | Gly   | Gln   | Val   | Lys   | Ser   | His   | Gly   | Asn   | Phe   | Thr   | Phe   | Met | Arg |
|       |       |       | 515   |       |       |       | 520   |       |       |       |       | 525   |       |     |     |
| Leu   | Tyr   | Gly   | Gly   | Gly   | His   | Met   | Val   | Pro   | Met   | Asp   | Gln   | Pro   | Glu   | Ser | Ser |
|       | 530   |       |       |       |       | 535   |       |       |       |       | 540   |       |       |     |     |
| Leu   | Glu   | Phe   | Phe   | Asn   | Arg   | Trp   | Leu   | Gly   | Gly   | Glu   | Trp   | Phe   |       |     |     |
| 545   |       |       |       |       | 550   |       |       |       |       | 555   |       |       |       |     |     |

( 2 ) INFORMATION FOR SEQ ID NO: 3:

( i ) SEQUENCE CHARACTERISTICS:
        ( A ) LENGTH: 2002 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Aspergillus niger ( i x ) FEATURE:
        ( A ) NAME/KEY: intron
        ( B ) LOCATION: 349..411

( i x ) FEATURE:
        ( A ) NAME/KEY: CDS
        ( B ) LOCATION: join (348..412)

( x i ) SEQUENCE DESCRIPTION: SEQ ID NO: 3:

```
GCGGCCGCTG CTACTTGCTT TTTCTAATTT GATACTTTTG TGTCCGTACC GTACCTTCCA      60

GACCGCAAGG TACCCATCCT CTACCTACTC ATCCCATCAT CATCTCGATT TCATACCAAC     120

CCCGTTGGGT TTCAACACA ATG AGA GTT CTT CCA GCT GCT ATG CTG GTT GGA     172
                    Met Arg Val Leu Pro Ala Ala Met Leu Val Gly
                     1               5                   10

GCG GGC ACT GCG GCC GTC CCT CCC TTC CAG CAG GTC CTT GGA GGT AAC      220
Ala Gly Thr Ala Ala Val Pro Pro Phe Gln Gln Val Leu Gly Gly Asn
          15                  20                  25
```

-continued

| | | | | | | | | | | | | | | | | |
|---|---|---|---|---|---|---|---|---|---|---|---|---|---|---|---|---|
| GGT | GCC | AAG | CAC | GGT | GCC | GAC | CAT | GCG | GCC | GAG | GTC | CCT | GCG | GAT | CAC | 268 |
| Gly | Ala | Lys | His | Gly | Ala | Asp | His | Ala | Ala | Glu | Val | Pro | Ala | Asp | His | |
| | | 30 | | | | 35 | | | | | 40 | | | | | |
| AGT | GCC | GAC | GGG | TTC | TCC | AAG | CCG | CTG | CAC | GCA | TTC | CAG | GAG | GAG | CTG | 316 |
| Ser | Ala | Asp | Gly | Phe | Ser | Lys | Pro | Leu | His | Ala | Phe | Gln | Glu | Glu | Leu | |
| 45 | | | | | 50 | | | | | 55 | | | | | | |
| AAG | TCT | CTC | TCT | GAT | GAG | GCT | CGT | AAG | CTG | TGG | GAT | GAG | GTT | GCT | AGC | 364 |
| Lys | Ser | Leu | Ser | Asp | Glu | Ala | Arg | Lys | Leu | Trp | Asp | Glu | Val | Ala | Ser | |
| 60 | | | | | 65 | | | | 70 | | | | | | 75 | |
| TTC | TTC | CCG | GAG | AGC | ATG | GAT | CAG | AAC | CCT | CTC | TTC | TCC | CTC | CCC | AAG | 412 |
| Phe | Phe | Pro | Glu | Ser | Met | Asp | Gln | Asn | Pro | Leu | Phe | Ser | Leu | Pro | Lys | |
| | | | | 80 | | | | 85 | | | | | | 90 | | |
| AAG | CAC | AAC | CGC | CGC | CCC | GAC | CAC | CAC | TGG | GAC | CAC | ATC | GTC | CGC | GGC | 460 |
| Lys | His | Asn | Arg | Arg | Pro | Asp | His | His | Trp | Asp | His | Ile | Val | Arg | Gly | |
| | | | 95 | | | | 100 | | | | | 105 | | | | |
| TCC | GAC | GTT | CAG | AGC | GTC | TGG | GTT | ACT | GGT | GAG | AAC | GGT | GAG | AAG | GAG | 508 |
| Ser | Asp | Val | Gln | Ser | Val | Trp | Val | Thr | Gly | Glu | Asn | Gly | Glu | Lys | Glu | |
| | | | 110 | | | | 115 | | | | 120 | | | | | |
| CGT | GAG | GTC | GAT | GGC | AAG | CTG | GAA | GCC | TAT | GAT | CTC | AGG | GTC | AAG | AAG | 556 |
| Arg | Glu | Val | Asp | Gly | Lys | Leu | Glu | Ala | Tyr | Asp | Leu | Arg | Val | Lys | Lys | |
| | 125 | | | | | 130 | | | | | 135 | | | | | |
| ACC | GAT | CCT | AGC | TCT | CTT | GGC | ATC | GAC | CCT | GGC | GTA | AAG | CAG | TAC | ACC | 604 |
| Thr | Asp | Pro | Ser | Ser | Leu | Gly | Ile | Asp | Pro | Gly | Val | Lys | Gln | Tyr | Thr | |
| 140 | | | | | 145 | | | | 150 | | | | | | 155 | |
| GGT | TAT | CTC | GAT | GAC | AAC | GAG | AAC | GAC | AAG | CAT | CTG | TTC | TAC | TGG | TTC | 652 |
| Gly | Tyr | Leu | Asp | Asp | Asn | Glu | Asn | Asp | Lys | His | Leu | Phe | Tyr | Trp | Phe | |
| | | | | 160 | | | | 165 | | | | | 170 | | | |
| TTC | GAG | TCT | CGC | AAT | GAC | CCC | GAG | AAT | GAC | CCT | GTT | GTT | CTG | TGG | CTG | 700 |
| Phe | Glu | Ser | Arg | Asn | Asp | Pro | Glu | Asn | Asp | Pro | Val | Val | Leu | Trp | Leu | |
| | | | 175 | | | | 180 | | | | | 185 | | | | |
| AAC | GGT | GGC | CCT | GGA | TGC | TCT | TCC | CTC | ACC | GGT | CTT | TTC | ATG | GAG | CTC | 748 |
| Asn | Gly | Gly | Pro | Gly | Cys | Ser | Ser | Leu | Thr | Gly | Leu | Phe | Met | Glu | Leu | |
| | | 190 | | | | | 195 | | | | 200 | | | | | |
| GGC | CCT | AGC | AGC | ATC | AAC | AAG | AAG | ATC | CAG | CCG | GTC | TAC | AAC | GAC | TAC | 796 |
| Gly | Pro | Ser | Ser | Ile | Asn | Lys | Lys | Ile | Gln | Pro | Val | Tyr | Asn | Asp | Tyr | |
| | 205 | | | | | 210 | | | | | 215 | | | | | |
| GCT | TGG | AAC | TCC | AAC | GCG | TCC | GTG | ATC | TTC | CTT | GAC | CAG | CCT | GTC | AAC | 844 |
| Ala | Trp | Asn | Ser | Asn | Ala | Ser | Val | Ile | Phe | Leu | Asp | Gln | Pro | Val | Asn | |
| 220 | | | | | 225 | | | | | 230 | | | | | 235 | |
| GTC | GGT | TAC | TCT | TAC | AGC | AAC | TCT | GCT | GTC | AGC | GAC | ACC | GTT | GCT | GCT | 892 |
| Val | Gly | Tyr | Ser | Tyr | Ser | Asn | Ser | Ala | Val | Ser | Asp | Thr | Val | Ala | Ala | |
| | | | | 240 | | | | 245 | | | | | 250 | | | |
| GGC | AAG | GAC | GTC | TAT | GCC | TTG | CTT | ACC | CTC | TTC | TTC | AAA | CAA | TTC | CCC | 940 |
| Gly | Lys | Asp | Val | Tyr | Ala | Leu | Leu | Thr | Leu | Phe | Phe | Lys | Gln | Phe | Pro | |
| | | | 255 | | | | | 260 | | | | | 265 | | | |
| GAG | TAT | GCC | AAG | CAG | GAC | TTC | CAC | ATT | GCC | GGT | GAA | TCC | TAT | GCT | GGT | 988 |
| Glu | Tyr | Ala | Lys | Gln | Asp | Phe | His | Ile | Ala | Gly | Glu | Ser | Tyr | Ala | Gly | |
| | | 270 | | | | | 275 | | | | | 280 | | | | |
| CAC | TAT | ATC | CCC | GTC | TTT | GCT | TCG | GAG | ATT | TTG | TCT | CAC | AAG | AAG | CGC | 1036 |
| His | Tyr | Ile | Pro | Val | Phe | Ala | Ser | Glu | Ile | Leu | Ser | His | Lys | Lys | Arg | |
| | 285 | | | | | 290 | | | | | 295 | | | | | |
| AAC | ATC | AAC | CTG | CAG | TCC | GTT | CTT | ATT | GGC | AAC | GGT | CTC | ACC | GAC | GGT | 1084 |
| Asn | Ile | Asn | Leu | Gln | Ser | Val | Leu | Ile | Gly | Asn | Gly | Leu | Thr | Asp | Gly | |
| 300 | | | | | 305 | | | | | 310 | | | | | 315 | |
| CTC | ACT | CAG | TAC | GAG | TAC | TAC | CGT | CCC | ATG | GCC | TGT | GGT | GAC | GGT | GGT | 1132 |
| Leu | Thr | Gln | Tyr | Glu | Tyr | Tyr | Arg | Pro | Met | Ala | Cys | Gly | Asp | Gly | Gly | |
| | | | | 320 | | | | 325 | | | | | 330 | | | |
| TAC | CCA | GCT | GTC | TTG | GAC | GAG | GGC | TCC | TGC | CAG | GCC | ATG | GAC | AAC | GCC | 1180 |
| Tyr | Pro | Ala | Val | Leu | Asp | Glu | Gly | Ser | Cys | Gln | Ala | Met | Asp | Asn | Ala | |
| | | | 335 | | | | | 340 | | | | | 345 | | | |

```
CTT CCT CGC TGC CAG TCT ATG ATT GAG TCT TGC TAT AGT TCC GAG AGC    1228
Leu Pro Arg Cys Gln Ser Met Ile Glu Ser Cys Tyr Ser Ser Glu Ser
        350                 355                 360

GCT TGG GTT TGT GTC CCG GCC TCC ATC TAC TGT AAC AAC GCC CTC CTT    1276
Ala Trp Val Cys Val Pro Ala Ser Ile Tyr Cys Asn Asn Ala Leu Leu
        365                 370                 375

GCC CCT TAC CAG CGC ACC GGA CAG AAC GTC TAC GAT GTT CGT GGT AAG    1324
Ala Pro Tyr Gln Arg Thr Gly Gln Asn Val Tyr Asp Val Arg Gly Lys
380                 385                 390                 395

TGC GAG GAT AGC TCC AAC CTC TGC TAC TCG GCC ATG GGC TAC GTC AGC    1372
Cys Glu Asp Ser Ser Asn Leu Cys Tyr Ser Ala Met Gly Tyr Val Ser
                400                 405                 410

GAC TAC CTG AAC AAG ACC GAG GTC ATT GAG GCT GTT GGC GCT GAG GTC    1420
Asp Tyr Leu Asn Lys Thr Glu Val Ile Glu Ala Val Gly Ala Glu Val
            415                 420                 425

AAC GGC TAC GAC TCG TGC AAC TTT GAC ATC AAC CGC AAC TTC CTC TTC    1468
Asn Gly Tyr Asp Ser Cys Asn Phe Asp Ile Asn Arg Asn Phe Leu Phe
        430                 435                 440

CAC GGT GAC TGG ATG AAG CCC TAC CAC CGT CTC GTT CCG GGA CTC CTG    1516
His Gly Asp Trp Met Lys Pro Tyr His Arg Leu Val Pro Gly Leu Leu
        445                 450                 455

GAG CAG ATC CCT GTC CTG ATC TAC GCT GGT GAC GCC GAT TTC ATC TGC    1564
Glu Gln Ile Pro Val Leu Ile Tyr Ala Gly Asp Ala Asp Phe Ile Cys
460                 465                 470                 475

AAC TGG CTG GGC AAC AAG GCC TGG ACT GAA GCC CTT GAG TGG CCC GGA    1612
Asn Trp Leu Gly Asn Lys Ala Trp Thr Glu Ala Leu Glu Trp Pro Gly
                480                 485                 490

CAG GCT GAA TAT GCC TCC GCT AAG CTG GAG GAC CTG GTC GTG GTC GAG    1660
Gln Ala Glu Tyr Ala Ser Ala Lys Leu Glu Asp Leu Val Val Val Glu
            495                 500                 505

AAT GAG CAC AAG GGC AAG AAG ATC GGC CAG GTC AAG TCC CAT GGC AAC    1708
Asn Glu His Lys Gly Lys Lys Ile Gly Gln Val Lys Ser His Gly Asn
        510                 515                 520

TTC ACC TTC ATG CGT CTC TAT GGC GGT GGC CAC ATG GTC CCG ATG GAC    1756
Phe Thr Phe Met Arg Leu Tyr Gly Gly Gly His Met Val Pro Met Asp
        525                 530                 535

CAA CCC GAG TCG AGT CTT GAA TTC TTC AAC CGC TGG TTG GGA GGT GAA    1804
Gln Pro Glu Ser Ser Leu Glu Phe Phe Asn Arg Trp Leu Gly Gly Glu
540                 545                 550                 555

TGG TTT TAA AGACGTGCTA TCACCGCATA TAGACTTTCC GGTCATTTCG GTGACACTGC 1863
Trp Phe

AGATATGTTT CTTAACGATA GTTTGAGGAT GCTTGTCAAT GCCCACTAAT CCCGAGCCTT   1923

ATGTTACATG GTATCTATGA GTTTGTCATT ATAGTGCATT ATGCATTTGT ACTCCGTACG   1983

AGAATGAATC AGCGGCCGC                                                2002
```

( 2 ) INFORMATION FOR SEQ ID NO: 4:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 4:

```
Met Arg Val Leu Pro Ala Ala Met Leu Val Gly Ala Gly Thr Ala Ala
1               5                   10                  15
```

-continued

| | | | | | | | | | | | | | | |
|---|---|---|---|---|---|---|---|---|---|---|---|---|---|---|
| Val | Pro | Pro | Phe | Gln | Gln | Val | Leu | Gly | Gly | Asn | Gly | Ala | Lys | His | Gly |
| | | | 20 | | | | | 25 | | | | | 30 | | |
| Ala | Asp | His | Ala | Ala | Glu | Val | Pro | Ala | Asp | His | Ser | Ala | Asp | Gly | Phe |
| | | 35 | | | | | 40 | | | | | 45 | | | |
| Ser | Lys | Pro | Leu | His | Ala | Phe | Gln | Glu | Glu | Leu | Lys | Ser | Leu | Ser | Asp |
| | | 50 | | | | | 55 | | | | | 60 | | | |
| Glu | Ala | Arg | Lys | Leu | Trp | Asp | Glu | Val | Ala | Ser | Phe | Phe | Pro | Glu | Ser |
| 65 | | | | | 70 | | | | | 75 | | | | | 80 |
| Met | Asp | Gln | Asn | Pro | Leu | Phe | Ser | Leu | Pro | Lys | Lys | His | Asn | Arg | Arg |
| | | | | 85 | | | | | 90 | | | | | 95 | |
| Pro | Asp | His | His | Trp | Asp | His | Ile | Val | Arg | Gly | Ser | Asp | Val | Gln | Ser |
| | | | 100 | | | | | 105 | | | | | 110 | | |
| Val | Trp | Val | Thr | Gly | Glu | Asn | Gly | Glu | Lys | Glu | Arg | Glu | Val | Asp | Gly |
| | | | 115 | | | | | 120 | | | | | 125 | | |
| Lys | Leu | Glu | Ala | Tyr | Asp | Leu | Arg | Val | Lys | Lys | Thr | Asp | Pro | Ser | Ser |
| | | 130 | | | | | 135 | | | | | 140 | | | |
| Leu | Gly | Ile | Asp | Pro | Gly | Val | Lys | Gln | Tyr | Thr | Gly | Tyr | Leu | Asp | Asp |
| 145 | | | | | 150 | | | | | 155 | | | | | 160 |
| Asn | Glu | Asn | Asp | Lys | His | Leu | Phe | Tyr | Trp | Phe | Phe | Glu | Ser | Arg | Asn |
| | | | | 165 | | | | | 170 | | | | | 175 | |
| Asp | Pro | Glu | Asn | Asp | Pro | Val | Val | Leu | Trp | Leu | Asn | Gly | Gly | Pro | Gly |
| | | | 180 | | | | | 185 | | | | | 190 | | |
| Cys | Ser | Ser | Leu | Thr | Gly | Leu | Phe | Met | Glu | Leu | Gly | Pro | Ser | Ser | Ile |
| | | 195 | | | | | 200 | | | | | 205 | | | |
| Asn | Lys | Lys | Ile | Gln | Pro | Val | Tyr | Asn | Asp | Tyr | Ala | Trp | Asn | Ser | Asn |
| | 210 | | | | | 215 | | | | | 220 | | | | |
| Ala | Ser | Val | Ile | Phe | Leu | Asp | Gln | Pro | Val | Asn | Val | Gly | Tyr | Ser | Tyr |
| 225 | | | | | 230 | | | | | 235 | | | | | 240 |
| Ser | Asn | Ser | Ala | Val | Ser | Asp | Thr | Val | Ala | Ala | Gly | Lys | Asp | Val | Tyr |
| | | | | 245 | | | | | 250 | | | | | 255 | |
| Ala | Leu | Leu | Thr | Leu | Phe | Phe | Lys | Gln | Phe | Pro | Glu | Tyr | Ala | Lys | Gln |
| | | | 260 | | | | | 265 | | | | | 270 | | |
| Asp | Phe | His | Ile | Ala | Gly | Glu | Ser | Tyr | Ala | Gly | His | Tyr | Ile | Pro | Val |
| | | 275 | | | | | 280 | | | | | 285 | | | |
| Phe | Ala | Ser | Glu | Ile | Leu | Ser | His | Lys | Lys | Arg | Asn | Ile | Asn | Leu | Gln |
| | 290 | | | | | 295 | | | | | 300 | | | | |
| Ser | Val | Leu | Ile | Gly | Asn | Gly | Leu | Thr | Asp | Gly | Leu | Thr | Gln | Tyr | Glu |
| 305 | | | | | 310 | | | | | 315 | | | | | 320 |
| Tyr | Tyr | Arg | Pro | Met | Ala | Cys | Gly | Asp | Gly | Gly | Tyr | Pro | Ala | Val | Leu |
| | | | | 325 | | | | | 330 | | | | | 335 | |
| Asp | Glu | Gly | Ser | Cys | Gln | Ala | Met | Asp | Asn | Ala | Leu | Pro | Arg | Cys | Gln |
| | | | 340 | | | | | 345 | | | | | 350 | | |
| Ser | Met | Ile | Glu | Ser | Cys | Tyr | Ser | Ser | Glu | Ser | Ala | Trp | Val | Cys | Val |
| | | | 355 | | | | | 360 | | | | | 365 | | |
| Pro | Ala | Ser | Ile | Tyr | Cys | Asn | Asn | Ala | Leu | Leu | Ala | Pro | Tyr | Gln | Arg |
| | 370 | | | | | 375 | | | | | 380 | | | | |
| Thr | Gly | Gln | Asn | Val | Tyr | Asp | Val | Arg | Gly | Lys | Cys | Glu | Asp | Ser | Ser |
| 385 | | | | | 390 | | | | | 395 | | | | | 400 |
| Asn | Leu | Cys | Tyr | Ser | Ala | Met | Gly | Tyr | Val | Ser | Asp | Tyr | Leu | Asn | Lys |
| | | | | 405 | | | | | 410 | | | | | 415 | |
| Thr | Glu | Val | Ile | Glu | Ala | Val | Gly | Ala | Glu | Val | Asn | Gly | Tyr | Asp | Ser |
| | | | 420 | | | | | 425 | | | | | 430 | | |
| Cys | Asn | Phe | Asp | Ile | Asn | Arg | Asn | Phe | Leu | Phe | His | Gly | Asp | Trp | Met |
| | | 435 | | | | | 440 | | | | | 445 | | | |

| | | | | | | | | | | | | | | |
|---|---|---|---|---|---|---|---|---|---|---|---|---|---|---|
| Lys | Pro 450 | Tyr | His | Arg | Leu | Val 455 | Pro | Gly | Leu | Leu | Glu 460 | Gln | Ile | Pro | Val |
| Leu 465 | Ile | Tyr | Ala | Gly | Asp 470 | Ala | Asp | Phe | Ile | Cys 475 | Asn | Trp | Leu | Gly | Asn 480 |
| Lys | Ala | Trp | Thr | Glu 485 | Ala | Leu | Glu | Trp | Pro 490 | Gly | Gln | Ala | Glu | Tyr 495 | Ala |
| Ser | Ala | Lys | Leu 500 | Glu | Asp | Leu | Val | Val 505 | Val | Glu | Asn | Glu | His 510 | Lys | Gly |
| Lys | Lys | Ile 515 | Gly | Gln | Val | Lys | Ser 520 | His | Gly | Asn | Phe | Thr 525 | Phe | Met | Arg |
| Leu | Tyr 530 | Gly | Gly | Gly | His | Met 535 | Val | Pro | Met | Asp | Gln 540 | Pro | Glu | Ser | Ser |
| Leu 545 | Glu | Phe | Phe | Asn | Arg 550 | Trp | Leu | Gly | Gly | Glu 555 | Trp | Phe | | | |

GENE ENCODING CARBOXYPEPTIDASE OF *ASPERGILLUS NIGER*

This is a divisional application of Ser. No. 08/309,341, filed Sep. 20, 1994, now U.S. Pat. No. 5,594,119, the contents of which are incorporated herein by reference in their entirety.

FIELD OF THE INVENTION

The present invention relates to a gene encoding a fungal vacuolar protease. In particular, the invention relates to a carboxypeptidase gene of a filamentous ascomycete or deuteromycete fungus, such as those of the genus Aspergillus.

BACKGROUND OF THE INVENTION

The fungal vacuole is an acidic organelle that contains many hydrolases, including several proteases, and is essentially equivalent to the mammalian lysosome. Several of the hydrolases have been identified and characterized in one or more species of fungi, particularly in yeast; these include protease A (PEP4 or PrA), protease B (PrB), aminopeptidase (APE), dipeptidyl aminopeptidase B (DPAP B), carboxypeptidase Y (CPY), and carboxypeptidase S (CPS). Most of the vacuolar hydrolases are glycoproteins which are synthesized as inactive precursors. In fact, all the aforementioned proteases with the exception of APE have signal peptides that lead to transit through the secretory pathway. In the late golgi, vacuolar proteins are sorted from secretory proteins and eventually delivered to the vacuole. In addition to a signal peptide, most vacuolar proteins also have a propeptide which is cleaved upon delivery to the vacuole to generate the mature active enzyme. It has been demonstrated that the amino acid information in PrA and CPY required for vacuolar targeting is present within the propeptide (Johnson et al., Cell 48: 875–885, 1987; Rothman et al. PNAS USA 83: 3248–3252, 1989; Valls et al., Cell 48: 887–897, 1989; Valls et al. J. Cell Biol. 111: 361–368, 1987). For CPY a string of four amino acid residues (QRPL) has been shown to be required for localization to the vacuole (Valls et al., J. Cell Biol. 111: 361–368, 1990). Once delivered to the vacuole, proteinase A (pep4) cleaves the propeptide of CPY and PrB leading to the activation of the proteases (Ammerer et al., Mol. Cell. Biol. 6: 2490–2499, 1986; Woolford et al., Mol. Cell. Biol. 6: 2500–2510, 1986).

In *S. cerevisiae*, three classes of mutants which mislocalize or missort vacuolar proteins have been identified (Bankaitis et al., PNAS USA 83: 9075–9079, 1986; Robinson et al., Mol. Cell. Biol., 8: 4936–4948, 1988; Rothman et al., EMBO J. 8: 2057–2065, 1989; Rothman and Stevens, Cell 47: 1041–1051, 1986). These mutants are called rids or vacuolar protein sorting mutants. Several of these mutants are isolated using a selection based on the observation that overexpression of a vacuolar protease due to a high copy number on a plasmid leads to a secretion of vacuolar proteases (Stevens et al., J. Cell Biol. 102: 1551–1557, 1986; Rothman et al, PNAS USA 83: 3248–3242, 1986). This suggests that it is possible to saturate the sorting machinery within the late golgi.

In *S. cerevisiae*, it has also been demonstrated that strains deleted for PEP4, CPY and PrB produce higher levels of heterologous proteins due to a decrease in proteolysis of the desired product. Therefore, the vacuolar proteases in question are important from a commercial point of view because many of the fungi which produce them are used for recombinant production of heterologous proteins. The presence of these proteases in fermentation is undesirable, in that they can degrade the protein of interest, thereby significantly reducing yield. Elimination of the function of any given protease is facilitated by the disruption or deletion of the gene encoding it; however, doing so first requires identification and isolation of the corresponding gene in the host species of interest. As noted above, a few such genes have been isolated from various yeast strains; however, the genes encoding vacuolar proteases in the filamentous ascomycetes or deuteromycetes are less well known. For example, PEPC (Frederick et al., Gene 125: 57–64, 1993) and PEPE (Jarai et al., Gene 145: 171–178, 1994) genes coding for two other vacuolar proteases from *Aspergilus niger* have been isolated. PEPC codes for a proteinase B(PrB) homologue, and PEPE codes for a proteinase A homologue. The gene PEP4 from *Neurospora crassa* coding for a PrA homologue has also been cloned (Bowman, 17th Fungal Genetics Conference, 1993). For the first time herein is described the gene encoding a vacuolar CPY from a filamentous ascomycete or deuteromycete.

SUMMARY OF THE INVENTION

The present invention relates to a nucleic acid construct comprising a sequence encoding a filamentous ascomycete or deuteromycete carboxypeptidase Y, as well as the recombinantly produced protein encoded thereby. As used herein, "nucleic acid construct" is intended to indicate any nucleic acid molecule of cDNA, genomic DNA, synthetic DNA or RNA origin. The term "construct" is intended to indicated a nucleic acid segment which may be single-or double-stranded, and which may be isolated in complete or partial form from a naturally occurring gene or which has been modified to contain segments of DNA which are combined and juxtaposed in a manner which would not otherwise exist in nature. The construct may optionally contain other nucleic acid segments. In a preferred embodiment, the sequence encodes a carboxypeptidase of the genus Aspergillus. The invention also provides a method for producing a non-carboxypeptidase-producing filamentous ascomycete or deuteromycete cell, which comprises disrupting or deleting the carboxypeptidase gene so as to prevent the expression of a functional enzyme, or treating the gene by classical mutagenesis using physical or chemical treatments to generate cells which are reduced or lacking in their ability to produce CPY. In addition, the invention also encompasses a filamentous ascomycete or deuteromycete which is unable to produce a functional carboxypeptidase enzyme, or which produces the carboxypeptidase in reduced amounts relative to the amount produced by the wild-type strain. Such organisms provide the basis for an improved method of recombinant protein production, wherein the carboxypeptidase-deficient microorganism is transformed with the nucleic acid construct encoding the protein of interest, and cultured under conditions conducive to the expression of the protein.

BRIEF DESCRIPTION OF THE FIGURES

FIG. 1 illustrates the DNA sequence and translation of the *A. niger* Bo-1 genomic CPY clone.

FIG. 2 illustrates the DNA sequence and translation of *A. niger* SFAG 2 CPY cDNA. The predicted site for signal peptidase cleavage and the N-terminus of mature CPY are indicated.

DETAILED DESCRIPTION OF THE INVENTION

Figure 3:
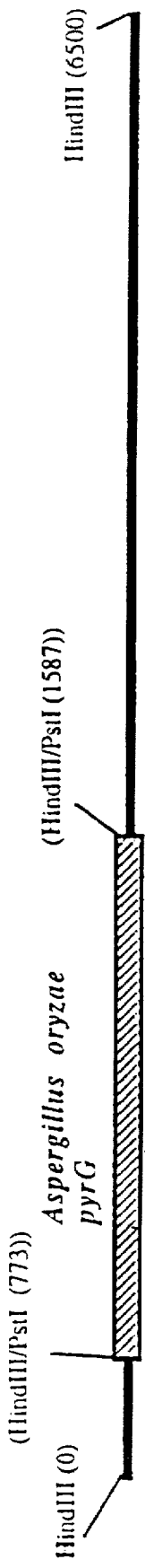
FIG. 3 illustrates the construct used in disruption CPY.

Attempts to isolate an Aspergillus carboxypeptidase Y are initiated by designing a series of degenerate oligonucleotides, using the sequences of *S. cerevisiae* CPY, *Penicillium janthinellum* carboxypeptidase S1 (Svedsen et al., FEBS 333: 39–43, 1993, and malt carboxypeptidase-MIII (Sørensen et al., Carlsberg Res. Commun. 54: 193–202, 1993). The oligonucleotide sequences are provided the examples below. These sequences are used as primers in various combinations in a PCR reaction using *Aspergillus niger* strain Bo-1 genomic DNA as a template. Two of the reactions (with primers 1-1 and 2-1; and 1-2 and 2-2) yield an 1100 bp amplification product, which is subcloned and sequenced, but none of the subclones has significant homology to CPY to be identified as the gene of interest.

Further PCR reactions with primers 3-1, 3-2, 4-1, 4-2, 2-1 and 2-2 are then made. In two of the reactions (primers 4-1 and 2-1; and 4-2 and 2-1) a 600 bp amplification product is obtained. This product is subcloned and 11 of the subclones sequenced; nine of these subclones are identical, and have homology to carboxypeptidaseY genes from other sources. The insert from one of the subclones is used to probe *A. niger* genomic DNA; hybridization with single bands is observed with BamHI, HindIII, and SalI digests, suggesting that a single CPY gene exists in *A. niger*. Hybridizations are done at 65° C. in 1.5×SSPE, 1.0% SDS, 0.5% non-fat milk and 200 µg/ml salmon sperm DNA.

An *A. niger* genomic DNA bank in EMBL4 is prepared and probed with the PCR CPY-derived gene fragment ($^{32}$P-labeled), in order to isolate a full length gene. Out of approximately 28,000 plaques, 11 positives are picked; nine of these still hybridize with the probe after purification. A 5.5 HindIII fragment common to a majority of these clones is identified as the *A. niger* CPY gene. This fragment is subcloned and sequenced; the sequence of the fragment, including the CPY coding region and predicted amino acid sequence, is provided in FIG. 1.

Subsequently, a cDNA bank from a different *A. niger* strain is also screened. At least one full-length clone is identified from this library as well. This clone is sequenced and the sequence is depicted in FIG. 2. Both DNA sequences predict a CPY precursor of 557 amino acids in length. Based on a comparison with the homologous gene from *S. cerevisiae*, CPY from *A. niger* appears to have a pre-propeptide of 137 or 138 amino acids. The gene contains one intron of 61 base pairs. A comparison of the two *A. niger* sequences will show some difference in amino acid sequence, which presumably reflects the different strains from which the genomic and cDNA clones are isolated. A comparison with the amino acid sequences of the corresponding CPY genes of *S. cerevisiae* and *C. albicans* shows a 65% and 66% identity, respectively.

The present invention is not limited to the use of the sequences disclosed in FIGS. 1 and 2. First, the invention also encompasses nucleotide sequences which produce the same amino acid sequence as depicted in FIG. 1 or 2, but differ by virtue of the degeneracy of the genetic code. In addition, the difference in amino acid sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In particular, the invention also encompasses any variant nucleotide sequence, and the protein encoded thereby, which protein retains at least about an 80%, preferably about 85%, and most preferably at least about 90–95% homology with the amino acid sequence depicted in FIG. 1 or 2, and which qualitatively retains the activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

In addition, the isolated gene provides a means for isolating homologous genes from other filamentous ascomycetes or deuteromycetes, such as other Aspergillus species, e.g., *A. oryzae*, *A. foetidus*, *A. japonicus*, *A. aculeatus*, or *A. nidulans*. Other non-Aspergillus filamentous ascomycete species include Fusarium species, such as *F. graminearum*, *F. oxysporum*, *F. solani*, *F. culmorum* (or corresponding teleomorphs) *Neurospora crassa*, *Trichoderma reesei*, *T. viridae*, *T. harzianum*, *T. longibranchiatum*, *Penicillium janthinellum*, *P. notatum*, *P. chrysogenum*, *P. camemberti*, *P. roqueforti*, *Humicola insolen*, *H. grisea* var. *thermoidea*, *H. lanuginosa*, *Scytalidium thermophilum*, *Myceliophthora thermophila*, and *Thielavia terrestris*. The gene, or an oligonucleotide based thereon, can be used as probes in southern hybridization to isolate homologous genes of these other species. In particular, such probes can be used under low to high stringency conditions (for example, prehybridization and hybridization at 42° C. in 5×SSPE, 0.3% SDS, 200 µg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding CPY gene therein. A PCR reaction using the degenerate probes mentioned herein and genomic DNA or first-strand cDNA from a filamentous fungus may also yield a CPY-specific product which could then be used as a probe to clone the corresponding genomic or cDNA.

The present gene is particularly useful in the creation of carboxypeptidase-deficient mutants of filamentous ascomycetes such as Aspergillus. This can be achieved in a number of ways. In one method, as described in further detail below, a selectable marker is cloned into the middle of the CPY gene. The disrupted fragment is then released from the parental plasmid using restriction enzymes. The linearized DNA fragment is used to transform the chosen host cell. In the host cell, the homologous ends pair with the host cell chromosome, and the homologous recombination results in a chromosomal gene replacement. Useful selectable markers for use with fungal cell hosts include amdS, pyrG, argB, niaD, sC, and hygB. Alternately, a two-step process can be employed using a two-way selectable marker. In such a process, a plasmid containing a truncated CPY gene and the selectable marker gene is digested with a restriction enzyme which cuts once within the the CPY fragment in order to target integration to the CPY locus during transformation. The transformants are then grown on media which will select for the loss of the selectable marker gene, e.g., when the marker is pyrG, the medium may contain 5-fluorootic acid. The loss of the selectable gene usually occurs by a recombination between the wild type CPY and the introduced truncated CPY gene. Approximately 50% of the resulting strain should have only the truncated CPY gene while the other 50% will contain only the wild type gene. Such methods are described in Rothstein, Meth. Enzymol. 194, 281–301, 1991.

The CPY-deficient mutants so created are particularly useful in the expression of heterologous protein. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the mutants involves the use of genetic elements not native to the host cell, or use of native elements which have been manipulated to function in a manner not normally seen in the host cell.

As already noted, the production of proteases by a chosen host cell can severely limit the yield of the desired protein by degrading the product before it can be recovered. The elimination or reduction in the amount of CPY produced by a host can therefore substantially increase the yield of any given protein, and can render an otherwise commercially unsuitable host cell commercially feasible for recombinant protein production. In a preferred embodiment, the CPY deficient cells produce at least 25% less, preferably at least 50% less, and most preferably at least 70% less CPY, up to total loss of CPY function, than the corresponding wild-type strain.

The mutant fungal cells of the present invention can be used in recombinant protein production in the same manner as the wild-type strains. Those skilled in the art will readily recognize routine variations from the specific embodiments described herein which are useful in adapting the methodology to the strains noted above. A gene of interest can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the sequence of the gene of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding A. oryzae TAKA amylase, Rhizomucor miehei aspartic proteinase, A. niger neutral α-amylase, A. niger acid stable α-amylase, A. niger or A. awamori glucoamylase (glaA), Rhizomucor miehei lipase, A. oryzae alkaline protease, A. oryzae triose phosphate isomerase or A. nidulans acetamidase. Preferred are the TAKA-amylase and glaA promoters.

The expression vector of the invention may also comprise a suitable transcription terminator and, in eukaryotes, polyadenylation sequences operably connected to the DNA sequence encoding the heterologous gene sequence. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of A. nidulans or A. oryzae. Furthermore, selection may be accomplished by co-transformation, e.g. as described in WO 91/17243.

It is generally preferred that the expression gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from Rhizomucor miehei, the gene for the α-factor from Saccharomyces cerevisiae or the calf preprochymosin gene. Particularly preferred, when the host is a fungal cell, is the preregion for A. oryzae TAKA amylase, A. niger neutral amylase, the maltogenic amylase form Bacillus NCIB 11837, B. stearothermophilus α-amylase, or Bacillus licheniformis subtilisin. An effective signal sequence is the A. oryzae TAKA amylase signal, the Rhizomucor miehei aspartic proteinase signal and the Rhizomucor miehei lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The CPY-deficient mutants can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The mutants can also be used to express heterologous proteins of pharmaceutical interest Such as hormones, growth factors, receptors, and the like.

The invention will be further illustrated by the following non-limiting examples.

EXAMPLES

I. Isolation of the *Aspergillus niger* CPY Gene

A. Materials and Methods i. Strains

The following biological materials are used in the procedures described below. *Escherichia coli* K802 (ek4-(nrca), mcrB, hsdR2, galK2, GalT22, supE44, metB1; *E. coli* SOLR(E14-(mcrA)Δ(mcrCB-hsdSMR-mr')171, sbcC, recB, recJ, uvrC, umuC::Tn5(kan'), lac, gyrA96, relA1, thi-1, endA1, λ$^R$[F'proABlacI$^q$ZΔM15]Su$^-$, *E. coli* JM101supE, thi-1, Δ(lacproAB), [F'traD36, proAB, lacI$^q$ZΔM15], *E. coli* XL-1 Blue recA1, endA1, gyrA96, thi-1, hsdR17, supE44, relA1, lac, [FproAB, lacI$^q$ZΔM15, Tn10(tet$^R$)], *Aspergillus niger* Bo-1, *A. niger* SFAG-2.

ii. PCR amplification

PCR reactions are run using standard protocols with annealing steps done at 45° C. *A. niger* Bo-1 genomic DNA is used as template and the following degenerate oligonucleotides are used.

Primer 1-1(94-282)-GGIGGICCIGGITGYTC
Primer 1-2(94-283)-GGIGGICCIGGITGYAG
Primer 2-1(94-284)-CCIAGCCARTTRCADAT
Primer 2-2(94-285)-CCYAACCARTTRCADAT
Primer 3-1(94-331)-GTIGGITTYTCITAYTCIGG
Primer 3-2(94-332)-GTIGGITTYAGYTAYAGYGG
Primer 4-1(94-329)-GARTCITAYGCIGGICAYTA
Primer 2-1(94-330)-GARAGYTAYGCIGGICAYTA In the above primers, I stands for inosine, Y for C or T, R for A or G, and D for A, G or T.

iii. Subcloning PCR products

PCR products are subcloned for sequencing using the TA Cloning Kit (Invitrogen) following the manufacturer's protocols.

iv. In vivo excision from Lambda Zap II

From the CPY cDNA Lambda Zap clones, a plasmid is rescued containing the cDNA inserts in a pBluescript SK-vector by passage through the *E. coli* strain SOLR following the protocols provided by Stratagene.

v. DNA sequencing

Nucleotide sequencing is determined using TAQ polymerase cycle-sequencing with fluorescent labeled nucleotides. The sequencing reactions are electrophoresed on an Applied Biosystems automatic DNA sequencer (Model 363A, version 1.2.0). The following CPY specific primers are used, in addition to the M13 reverse (−48) and M13 (−20) forward primers (Sanger et al., J. Mol. Biol. 143: 163–178):

| | |
|---|---|
| 94-376 | TCGCTGCCAGTCTATGATTGA |
| 94-377 | ACATCAACCGCAACTTCCTCT |
| 94-378 | TTGCCAATGAGAACGGACTGC |
| 94-379 | CGCACTTACCACGGACATCAT |
| 94-503 | CAAGCATCCTCAAACTATCGT |
| 94-504 | GAGACGCATGAAGGTGAAGTT |
| 94-505 | GCCGTCCCTCCCTTCCAGCAG |
| 94-506 | GTGCCGACGGGTTCTCCAAGC |
| 94-507 | GCAGCGAGGAAGAGCGTTGTC |
| 94-510 | GGGTCATTCTCGGGGTCATTG |
| 94-511 | GACCCCGAGAATGACCCTGTT |
| 94-512 | GTAGGGCTTCATCCAGTCACC |
| 94-513 | TCTCACCGTTCTCACCAGTAA |
| 94-514 | TCCCTCCCCAAGAAGCACAAC |
| 94-528 | AGCGTCTGGGTTACTGGTGAG |
| 94-529 | AAGATCGGCCAGGTCAAGTCC |
| 94-530 | GAGACGGTGGTAGGGCTTCAT |
| 94-531 | AACGTCGGTTACTCTTACAGC |
| 94-532 | GTQGTCGGGGCGGCGGTTGTG |
| 94-533 | TGTTTGAAGAAGAGGGTAAGC |
| 94-575 | CGCTGCTACTTGATTTTTCTA |
| 94-576 | CTCAGCGCCAACAGCCTCAAT |
| 94-577 | ACCTGCAGTCCGTTCTTATTG |
| 94-634 | TGCGATCGATTCATTCTCATC |
| 94-635 | GGAGTAACCGACATTGACAGG |
| 94-636 | CCTGTCAATGTCGGTTACTCC |
| 94-637 | GTCCCATGGCAACTTCACCTT |
| 94-646 | CTTCTCACCGTTCTCACCAGT |
| 94-647 | CGAGACTCGAAGAACCCTAAG |

B. Results

Using *A. niger* Bo-1 genomic DNA as template PCR reactions are done using various combinations of the CPY specific degenerate oligonucleotides, primers 1-1, 1-2, 2-1, and 2-2 (FIG. 1). All reactions are done using one cycle at 95° C. for 5 minutes, 45° C. for 1 minute and 72° C. for 2 minutes followed by 25 cycles at 95° C. for 1 minute, 45° C. for one minute and 72° C. for 2 minutes. Aliquots (10 μl) of the reactions were electrophoresed on an agarose gel, and in two of the reactions, one with primers 1-2 and 2-1 and one with primers 1-2 and 2-2, an amplification product of approximately 1100 bp is the major species. The predicted size of a product using these oligonucleotide combinations assuming there are no introns within the gene is 900 bp. the 1100 bp amplification product is subcloned and sequenced using the forward and reverse primers. Seven of the subclones are sequenced; however, none of them by homology code for CPY.

PCR reactions using various combinations of primers 3-1, 3-2, 4-1, 4-2, 2-1 and 2-2 are run using the same conditions as above. Aliquots are electrophoresed on an agarose gel, and in two of the reactions, one with primers 4-1 and 2-1 and one with primers 4-2 and 2-1, an amplification product of approximately 600 bp is the major species. The expected size for this amplification product based on homology to other carboxypeptidases is 600 bp. The 600 bp amplification product is subcloned and the DNA sequence is determined for 11 of the subclones Using the forward and reverse primers. Nine of the 11 subclones, based on identity of 69% to *S. cerevisiae*, code for CPY from *A. niger*. All 9 are identical to one another suggesting there is only one gene for carboxypeptidase in *A. niger*. The subclone containing the *A. niger* CPY PCR product of 600 bp is designated pDSY17.

A Southern blot of *A. niger* Bo-1 genomic DNA is probed with the insert from pDSY17. The probe is radiolabeled using a nick-translation kit from Gibco-BRL. Hybridization conditions used are 60° C. in 1.5×SSPE, 1% SDS, 0.5% nonfat milk and 200 μg/ml salmon sperm DNA. The blot is washed at 65° C. for 15 minutes twice in 0.2×SSC, 1% SDS and 0.1% Na pyrophosphate. In the BamHI, HindIII and SAlI digests, single bands of approximately 10, 5.5 and 7 kb, respectively hybridize to the CPY probe.

In order to isolate the full gene for CPY, a genomic bank in EMBL4 of *A. niger* Bo-1 containing approximately 26,000 recombinants is probed with the PCR-derived CPY gene fragment, radiolabeled with the Gibco-BRL nick translation kit. Approximately 28,000 plaques are lifted to filters and probed. Eleven positives from these plates are picked. After purification, 9 of the primary clones still hybridized with the CPY probe. DNA is isolated from the 9 clones, and restriction digests are done in order to begin characterizing them. From the restriction patterns, 7 of the 9 are identical. The other two clones are unique. From Southern digests of the clones, it is determined that 8 of the 9 have the same HindIII fragment of approximately 5.5 kb which hybridizes to the CPY probe. The clone which does not contain the same HindIII fragment contains a larger (>12 kb) HindIII fragment which hybridizes to the CPY probe. The Common HindIII fragment is subcloned for DNA sequencing. The genomic DNA sequence and predicted amino acid sequence is shown in FIG. 1.

A cDNA bank in Lambda ZAPII (Stratagene) of *A. niger* SFAG-2 is also screened. Approximately 42,000 plaques are lifted to filter and probed with the CPY probe as above, and 112 of these plaques appear to hybridize under the stringent conditions defined above. Twenty of the initial positives are picked and rescreened, and upon purification, 18 still hybridize with the CPY probe. From 4 of the positive clones, DNA is isolated using the in vivo excision protocol provided with the Lambda zap kit. The rescued plasmids are digested with EcoRI and electrophoresed on an agarose gel to determine the sizes of the inserts. Two of the clones (2-1 and 3-2) appear to have large enough inserts to contain the full length cDNA for CPY, and each contains two EcoRI fragments of approximately 1700 and 250 bp. The predicted size for a full length cDNA is approximately 1600 bp. The other two cDNA clones (2-2 and 2-4) have smaller inserts; however, they all contain the 250 bp EcoRI fragment. Partial DNA sequences of clones 3-2 and 2-2 are determined, and 3-2 contains the full-length cDNA while clone 2-2 is truncated at the 5' end by about 200 bp.

The complete cDNA sequence is determined on both strands (FIG. 2). The cDNA is predicted to code for a CPY precursor of 557 amino acids in length. To date most of the nucleotide differences found between the cDNA and genomic clones are within the wobble which is not surprising since they come from two different *A. niger* strains. Based on an alignment with CPY from *S. cerevisiae*, CPY from *A. niger* appears to have both a signal peptide and a propeptide and the mature CPY protein is either 419 or 420 amino acids in length. *A. niger* CPY has approximately 65% and 66% identity to CPY from the yeasts *S. cerevisiae* and *C. albicans* (Mukhtar et al., Gene 121: 173–177, 1992), respectively.

II. Preparation of a CPY-Deficient Mutant

In order to create an *A. niger* strain deleted for CPY, a construct in which the *A. oryzae* pyrG gene is inserted into the coding region of CPY is made (FIG. 3). An ~6.5 kb HindIII fragment containing almost the entire gene of CPY and ~6 kb downstream of the gene is subcloned into a pKS+ (Stratagene) derivative in which the PstI site has been destroyed. The resulting recombinant is digested with PstI to delete an 815 bp fragment from the CPY coding region, and the overhangs created by digestion with PstI are blunted by the addition of T4 DNA polymerase and all 4 dNTPs. The resulting blunt-end vector is ligated to an ~3.8 kb blunt-end fragment obtained by digestion with HindIII followed by a fill-reaction using Klenow fragment. The final construct in which the CPY gene has the pyrG inserted is digested with HindIII to create a linear fragment which is used to transform an *A. niger* pyrG strain selecting for growth on minimal medium plates. Transformants are screened by Southern blotting to determine which strains contain a disrupted CPY gene. The transformants are further analyzed by Western blotting to look for the absence of CPY intracellularly. Once a strain is identified as containing a disruption of CPY, the effect on heterologous protein is determined.

Deposit of Biological Materials

The following biological materials have been deposited on Sep. 13, 1994 in Agricultural Research Service Culture Collection (NRRL) 1815 North University Street, Peoria, Ill. 61664.

| Cell line | Accession No. |
|---|---|
| *E. coli* containing pDSY23 (EMCC #0120) | NRRL B-21326 |

What is claimed is:

1. A mutant filamentous ascomycete cell which produces at least 25% less carboxypeptidase Y than a corresponding wild-type cell when cultured under identical conditions, wherein the endogenous carboxypeptidase Y gone has been replaced by homologous recombination with a nucleic acid sequence wherein the nucleic acid sequence is selected from the group consisting of (i) the nucleic acid sequence depicted in SEQ ID NO:1 or SEQ ID NO:3 and (ii) a nucleic acid sequence which hybridizes with SEQ ID NO:1 or SEQ ID NO:3 under high stringency conditions; which sequence has been disrupted.

2. The cell of claim 1 which produces 50% less carboxypeptidase Y than a corresponding wild-type cell.

3. The cell of claim 1 which produces at least 70% less carboxypeptidase Y than a corresponding wild-type cell.

4. The cell of claim 1, wherein the nucleic acid Sequence which has been disrupted is the nucleic acid sequence depicted in SEQ ID NO:1.

5. The cell of claim 1, wherein the nucleic acid sequence which has been disrupted is the nucleic acid sequence depicted in SEQ ID NO:3.

6. The cell of claim 1, wherein the nucleic acid sequence which has been disrupted is a nucleic acid sequence which hybridizes with SEQ ID NO:1 under high stringency conditions.

7. The cell of claim 1, wherein the nucleic acid sequence which has been disrupted is the nucleic acid sequence which hybridizes with SEQ ID NO:3 under high stringency conditions.

8. The cell of claim 1, wherein the nucleic acid sequence has been disrupted by insertion of a selectable marker.

9. The cell of claim 8, wherein the selectable marker is amdS, pyrG, argB, niaD, sC, or hygB.

10. The cell of claim 1 which is selected from the group consisting of Aspergillus, Fusarium, Humicola, Myceliophthora, Penicillium, Trichoderma, Scytalidium, Trichoderma, Thielavia.

11. The cell of claim 10 which is *Aspergillus niger*.

* * * * *